United States Patent [19]

Apeldoorn et al.

[11] Patent Number: 5,444,162
[45] Date of Patent: Aug. 22, 1995

[54] MIXTURE OF DISACCHARIDE ESTERS OF 3-METHYLPENTANOIC ACID AND ACETIC ACID FOR FLAVOURING

[75] Inventors: Willem Apeldoorn, Amsterdam; Harrie Renes, Nederhorst den Berg; Hans J. Wille, Bussum, all of Netherlands

[73] Assignee: Unilever Patent Holdings B.V., Vlaardingen, Netherlands

[21] Appl. No.: 956,320

[22] Filed: Oct. 5, 1992

[30] Foreign Application Priority Data

Oct. 5, 1991 [EP] European Pat. Off. ............ 91202599

[51] Int. Cl.⁶ ................ A24F 47/00; A24B 15/00; A23L 2/26; C07H 11/00
[52] U.S. Cl. ............................ 336/115; 131/347; 131/352; 126/534; 536/119; 536/123.13
[58] Field of Search ............ 536/64, 71, 32, 64, 536/71, 107, 119, 115, 123.13; 426/534, 538; 131/347, 352

[56] References Cited

U.S. PATENT DOCUMENTS

| | | | |
|---|---|---|---|
| 2,245,208 | 6/1941 | Malm et al. | 536/64 |
| 2,534,371 | 12/1950 | Richter et al. | 536/64 |
| 2,682,534 | 6/1954 | Hewson et al. | 536/64 |
| 3,096,324 | 7/1963 | Goins et al. | 260/234 |

OTHER PUBLICATIONS

Garegg et al, Carbohydrate Research, 181:89–96 (1988).
Severson et al, J. Agric. Food Chem., 33:870–875 (1985).
Abstract of JP-A-02.203775.
Patent Abstracts of Japan, vol. 15, No. 429 (Oct. 1991) and JP-A-31 78 989 (Aug., 1991).
Nishida et al, Journal of the Chemical Society, Chemical Communications, No. 13, pp. 998–1000 (Jul., 1986).
Wahberg et al, Acta Chemica Scandinavica, B40(9):724–730 (Oct. 1986).
Gareggg et al, Carbohydrate Research, 181:89–96 (Oct. 1988).
Severson et al, Journal of Agricultural and Food Chemistry, 33:870–875 (1985).
Patent Abstracts of Japan, vol. 14, No. 492 (Jan. 1990) and JP-A-22 03 775 (Aug., 1990).

*Primary Examiner*—David M. Naff
*Assistant Examiner*—Deborah K. Ware
*Attorney, Agent, or Firm*—Cushman, Darby & Cushman

[57] ABSTRACT

A mixture of disaccharide esters of 3-methylpentanoic and acetic acid is prepared and used as flavor precursors. The esters average at least 4 and preferably at least 4.5 3-methylpentanoyl groups per disaccharide moiety, with remaining positions being substantially occupied by acetyl groups. Suitable disaccharides are sucrose and lactose. Preferably the disaccharide ester has an acetyl/methylpentanoyl group ratio of about 2.3 to 3.2:4.8 to 5.7. The disaccharide esters are suitable for flavoring products undergoing a heating step during preparation or consumption, such as ingredient mixes for extrusion, frying or baking, and especially tobacco. On heating they liberate 3-methylpentanoic acid and/or its decomposition products.

13 Claims, No Drawings

MIXTURE OF DISACCHARIDE ESTERS OF 3-METHYLPENTANOIC ACID AND ACETIC ACID FOR FLAVOURING

The invention is concerned with disaccharide esters of 3-methylpentanoic acid and with their use as flavour precursors.

In the art of flavouring it is known to use so called precursor compounds which themselves do not have the desired organoleptic properties, but which decompose under the conditions of preparation or consumption of the flavoured product, thus liberating a desired flavour component which then contributes to the flavour of the product. Also, such precursors may already be naturally present in a product. Thus, 6-O-acetyl-2,3,4-tri-O-(3-methylpentanoyl)sucrose was identified as a flavour precursor in various tobaccos, cf. P. J. Garegg et al, Carbohydrate Research, 181 (1988) 89–96 and R. F. Severson et al, J.Agric. Food Chem., 33 (1985) 870–875. On the other hand, acetyl-tri-O-acyl-glucose, wherein the acyl groups may have 2–8 carbon atoms provided one of them is 2-methylbutenoyl, have been described in JP-A-02.203775 as constituents of wild tobacco plants and contributing to tobacco flavour.

However, there is a continuous need for new stable flavour precursors, which are relatively non-volatile, reasonably thermostable and which on decomposition give a high yield of the desired flavour. Also, the flavour precursor should preferably be easy to prepare.

It has now been found that mixed disaccharide esters of 3-methylpentanoic acid and acetic acid containing on average at least 4 3-methylpentanoyl groups per disaccharide moiety are excellent flavour precursors which on heating liberate 3-methylpentanoic acid in high yields. Preferably, the average number of 3-methylpentanoyl groups in the disaccharide esters is at least 4.5, with the remaining positions being substantially occupied with acetyl groups. Suitable disaccharides are e.g. sucrose and lactose. The preferred saccharide is sucrose.

Other disaccharide esters are known and used for various purposes, see e.g. U.S. Pat. No. 3,096,324. However, the disaccharide esters according to the invention are novel. They may be prepared according to procedures known in the art for other saccharide esters, e.g. as described in U.S. Pat. No. 3,096,324. A suitable procedure comprises treatment of the saccharide with a mixture of 3-methylpentanoic acid anhydride and acetic acid anhydride in the presence of barium salts. The reaction product obtained generally comprises a mixture of esters having the acetyl and methyl-pentanoyl groups in different positions in the disaccharide moiety and having different numbers of acetyl and methyl-pentanoyl groups in the ester molecule. The average ratio of acetyl and methylpentanoyl groups in the disaccharide esters in this mixture depends on the molar ratio of acetic and methylpentanoic acid anhydride used as starting materials. In general a large excess of methylpentanoic acid anhydride on disaccharide and on acetic acid anhydride is used.

Thus, as indicated, the value given above for the required number of methylpentanoyl groups per dissacharide moiety should be taken as an average. Mixtures of esters having the right average values may include compounds actually having less than 4 methylpentanoyl groups per disaccharide moiety. The various components of the reaction product may be separated using standard separation techniques known in the art. However, such separation is superfluous for the use of the esters as flavour precursors and therefore the product mixture can be used as such.

The disaccharide esters according to the invention are suitable as precursors for 3-methyl-pentanoic acid in all products which during preparation or consumption undergo a rise in temperature of sufficient magnitude to effectively liberate 3-methyl-pentanoic acid. They may be added to products to be flavoured, either as such, or as part of a flavour composition. The term flavour composition as used herein means a mixture of flavour components, if desired dissolved in a suitable solvent or mixed with a powdered substrate or carrier or processed to form a powdered product. Such flavour composition is used to impart a flavour to a product or to improve or alter the flavour a product already has. Examples of products the esters may be added to, either as such or as part of a flavour composition, are ingredient mixes for products which are prepared by extrusion, frying or baking. The esters are especially suitable for flavouring tobacco, whereby the methylpentanoic acid is liberated during the smoking process. For the purposes of this invention the term tobacco is used generically to describe tobacco itself, including reconstituted tobacco and tobacco substitutes, as well as shaped articles containing tobacco, such as cigarettes, cigars and the like and also articles, whether or not containing real tobacco, which are intended to give a sensation akin to smoking tobacco.

Flavour components which may be advantageously combined with the esters according to the invention are: natural products such as extracts, essential oils, absolutes, resins, concretes, fruit juices, etc., but also synthetic components such as hydrocarbons, alcohols, aldehydes, ketones, esters, ethers, acetals, ketals, acids, etc., including saturated and unsaturated compounds, aliphatic, alicyclic and heterocyclic compounds. Such flavour components are mentioned, for example, in S. Arctander, Perfume and Flavor Chemicals (Montclair, N.J., 1969), in S. Arctander, Perfume and Flavor Materials of Natural Origin (Elizabeth, N.J., 1960), in T. E. Furia et al., CRC Fenaroli's Handbook of Flavor Ingredients, 2nd edition (Cleveland, CRC Press Inc., 1975), H. B. Heath, Source Book of Flavours, The Avi Publishing Co. Inc. Westport, Conn. (1981) and in "Flavor and Fragrance Materials—1989", Allured Publishing Co. Wheaton, Ill. USA. Auxiliary substances and solvents which can be used in flavour compositions containing the esters according to the invention are, for example: ethanol, isopropanol, diethyleneglycol monoethyl ether, glycerol, triacetin etc. Powdered substrates or carriers may include salt, starch derivatives and the like. Processing into a powdered product may include spray-drying and other techniques of micro-encapsulation.

The quantities of the esters according to the invention to be used for flavouring a product may be strongly divergent and depend, inter alia, on the type of product wherein the esters are used, on the nature and the quantity of the other components of a flavour composition and on the intended flavour effect. In most cases the esters according to the invention will already have a clearly perceptible organoleptic effect when present in a product in an amount of 0.01 ppm by weight or more. Generally they will be used in amounts of 0.5 ppm or more. Depending on the amount of flavour composition intended to be added to a product to be flavoured, the amount of disaccharide esters in a flavour compositions will generally be 1 ppm by weight or more.

A number of ways are known in the art for applying the esters according to the invention (either as such or as a part of a flavour composition) to products to be flavoured, strongly depending on the specific nature of the product. In the case of tobacco, methods for applying flavours or flavour compositions include simply spraying or atomizing the flavour or flavour composition (diluted with a suitable solvent like alcohol if desired) over the bulk of the tobacco. Another method may be finely dispersing an emulsion over the bulk of the tobacco, wherein the emulsion may comprise an emulsifier, an aqueous phase, and an oil phase. Other components may be included in such emulsions. Such a method is described in more detail in EP-A-366 835. According to still another method for applying the flavour components to tobacco they are micro-encapsulated and subsequently mixed with the tobacco bulk. Optionally an adhesive may be used to fix the microcapsules to the tobacco leaf.

The following examples are given to illustrate the invention, which is, however, not in any way limited thereto.

EXAMPLE 1

Preparation of Sucrose Esters

3-Methylpentanoic acid anhydride was prepared from 6 moles of 3-methylpentanoic acid and 4.5 moles of acetic acid anhydride, by distilling acetic acid and the excess acetic acid anhydride from the reaction mixture at atmospheric pressure to a pot temperature of 220° C. Thereafter the desired anhydride was purified by distillation under reduced pressure. Yield: 97% of theory.

A one liter reaction flask, equipped with a mechanical stirrer, a reflux condensor, a nitrogen inlet tube and a thermometer was charged with 3 moles of 3-methylpentanoic acid anhydride, 0.3 moles of acetic acid anhydride, 0.3 moles of sucrose and 6 g of barium hydroxide.8 aq. This mixture was stirred under nitrogen at 130° C. until all sucrose was dissolved (about 6 hours). Thereafter the mixture was distilled under reduced pressure (0.3 kPa) until a pot temperature of 175° C. was reached, whereby 487 g of distillate was obtained comprising 61% w/w 3-methylpentanoic acid and 38% of the corresponding anhydride. The 284 g concentrate, which contained a precipitate of barium salts, was dissolved in 300 g of cyclohexane and 1 mole of methanol was added. The mixture was heated to 60° C. for 15 minutes, cooled to ambient and mixed with 100 ml 10% acetic acid solution. The water layer was separated and the organic layer successively washed with 100 ml of water, 100 ml of 10% sodium carbonate solution, 100 ml of 5% sodium carbonate solution and again 100 ml of water. Thereafter the cyclohexane was thoroughly removed by evaporation to a final pressure of 0.3 kPa at 90° C. Thus, 268 g (89% of theory) of sucrose acetate 3-methylpentanoate was obtained having an acetyl/methylpentanoyl group ratio of 2.3:5.7.

The procedure was repeated using a molar ratio methylpentanoic acid anhydride: acetic acid anhydride:sucrose=9:2:1 instead of the 10:1:1 above. The product obtained (93% of theory) had an acetyl/methylpentanoyl group ratio of 3.2:4.8.

EXAMPLE 2

An oriental tobacco type flavour composition was prepared according to the following recipe:

|  | parts by weight |
|---|---|
| γ-Butyrolactone | 250 |
| Benzyl alcohol | 220 |
| Ethyl palmitate | 200 |
| γ-Valerolactone | 60 |
| Acetic acid | 30 |
| Ethyl decanoate | 30 |
| Ethyl laurate | 25 |
| Coffee extract | 25 |
| Farnesol | 20 |
| γ-Heptalactone | 15 |
| Malt extract | 10 |
| Furfural | 5 |
| Acetophenone | 4 |
| Guajacol | 3 |
| Clary sage oil | 2 |
| Benzaldehyde | 1 |
| Sucrose acetate methylpentanoate according to Example 1 | 100 |
| Total | 1000 |

This flavour composition is suitable for imparting an oriental tobacco-type flavour to low grade or low flavour tobacco. It may be used as a 5% solution in ethanol to be sprayed over tobacco.

We claim:

1. Mixture of disaccharide ester molecules of 3-methylpentanoic acid and acetic acid, wherein each disaccharide ester molecule includes one disaccharide moiety and eight acyl moieties, said acyl moieties being on average at least 4 3-methylpentanoyl groups per single disaccharide moiety, with remaining positions on the acyl moieties being occupied by acetyl groups to provide an acetyl/methylpentanoyl group ratio of about 2.3 to 3.2:4.8 to 5.7.

2. Mixture of disaccharide ester molecules according to claim 1 wherein the average number of 3-methylpentanoyl groups per single disaccharide moiety is at least 4.5.

3. Mixture of disaccharide ester molecules according to claim 1 wherein the disaccharide moiety is comprised of sucrose or lactose.

4. Flavoured products containing a product and a mixture of disaccharide ester molecules of 3-methylpentanoic acid and acetic acid, wherein each disaccharide ester molecule includes one disaccharide moiety and eight acyl moieties, said acyl moieties being on average at least 4 3-methylpentanoyl groups per single disaccharide moiety, with the remaining positions on the acyl moieties being occupied by acetyl groups to provide an acetyl/methylpentanoyl group ratio of about 2.3 to 3.2:4.8 to 5.7.

5. Flavoured products according to claim 4 wherein the average number of 3-methylpentanoyl groups per single disaccharide moiety is 4.5.

6. Flavoured products according to claim 4 wherein the disaccharide moiety is comprised of sucrose or lactose.

7. Flavoured products according to claim 4 wherein the disaccharide ester molecules are present in an amount of at least 0.01 ppm by weight.

8. Flavoured products according to claim 7 wherein the disaccharide moiety is comprised of sucrose or lactose.

9. Flavouring compositions comprising flavour components and a mixture of disaccharide ester molecules of 3-methylpentanoic acid and acetic acid, wherein each disaccharide ester molecule includes one disaccharide moiety and eight acyl moieties, said acyl moieties being on average at least 4 3-methylpentanoyl groups per single disaccharide moiety, with the remaining positions on the acyl moieties being occupied by acetyl groups to provide an acetyl/methylpentanoyl group ratio of about 2.3 to 3.2:4.8 to 5.7.

10. Flavouring compositions comprising flavour components and a mixture of disaccharide ester molecules of 3-methylpentanoic acid and acetic acid, wherein each disaccharide ester molecule includes one disaccharide moiety and eight acyl moieties, said acyl moieties being on average at least 4.5 3-methylpentanoyl groups per disaccharide moiety, with the remaining positions on the acyl moieties being occupied by acetyl groups to provide an acetyl/methylpentanoyl group ratio of about 2.3 to 3.2:4.8 to 5.7.

11. Flavoring compositions according to claim 10 wherein the disaccharide moiety is comprised of sucrose or lactose.

12. Tobacco products containing tobacco and a mixture of disaccharide ester molecules of 3-methylpentanoic acid and acetic acid, wherein each disaccharide ester molecule includes one disaccharide moiety and eight acyl moieties, said acyl moieties being on average at least 4 3-methylpentanoyl groups per single disaccharide moiety, with the remaining positions on the acyl moieties being occupied by acetyl groups to provide an acetyl/methylpentanoyl group ratio of about 2.3 to 3.2:4.8 to 5.7.

13. Tobacco products according to claim 12, wherein the disaccharide ester molecules are present in an amount of at least 0.01 ppm by weight.

* * * * *